US012582743B2

(12) United States Patent
Kushnir et al.

(10) Patent No.: US 12,582,743 B2
(45) Date of Patent: Mar. 24, 2026

(54) BLOOD EXTRACTION

(71) Applicant: Reddress Ltd, Pardes Hana (IL)

(72) Inventors: Alon Kushnir, Givat Ada (IL); Ohad Ilan, Givat Ada (IL)

(73) Assignee: REDDRESS LTD., Pardes Hana (IL)

( * ) Notice: Subject to any disclaimer, the term of this patent is extended or adjusted under 35 U.S.C. 154(b) by 825 days.

(21) Appl. No.: 17/917,025

(22) PCT Filed: Apr. 7, 2021

(86) PCT No.: PCT/IL2021/050404
§ 371 (c)(1),
(2) Date: Oct. 5, 2022

(87) PCT Pub. No.: WO2021/205457
PCT Pub. Date: Oct. 14, 2021

(65) Prior Publication Data
US 2023/0158201 A1     May 25, 2023

(30) Foreign Application Priority Data

Apr. 7, 2020     (IL) .......................................... 273876

(51) Int. Cl.
*A61F 13/00* (2024.01)
*A61L 15/40* (2006.01)
(52) U.S. Cl.
CPC ........ *A61L 15/40* (2013.01); *A61F 13/00987* (2013.01)
(58) Field of Classification Search
CPC ............... A61L 15/40; A61L 2300/418; A61L 26/0057; A61F 13/00987; A61F 13/01;
(Continued)

(56) References Cited

U.S. PATENT DOCUMENTS

| 4,327,746 A | 5/1982 | Feaster |
| 6,110,160 A | 8/2000 | Faerber |
| (Continued) | | |

FOREIGN PATENT DOCUMENTS

| CA | 2811822 A1 | 3/2012 |
| CN | 03819169 A | 9/2005 |
| (Continued) | | |

OTHER PUBLICATIONS

International Search Report for corresponding application PCT/IL2021/050404 filed Apr. 7, 2021; Mail date Jun. 27, 2021.
(Continued)

*Primary Examiner* — Susan S Su
(74) *Attorney, Agent, or Firm* — CANTOR COLBURN LLP

(57) ABSTRACT

The present invention relates to a container (1, 10) for holding a liquid, in particular an infusion or irrigation liquid, said container having a liquid phase (6) containing the liquid and a gas phase (4), in which in the operating position a liquid opening is formed in the lower region of the container (1, 10) and the container has a gas opening. The gas opening is formed by a gas pipe (3) permanently connected to the container (1, 10) and having a first gas pipe end (12) and a second gas pipe end (13). The first gas line end (12) extends into the gas phase (4) of the vessel (1, 10) and is provided with a fastener. The second gas pipe end (13) opens to the outside of the vessel (1, 10).

19 Claims, 7 Drawing Sheets

(58) Field of Classification Search
CPC .... A61F 2013/0017; A61F 2013/00412; A61F 2013/00417; A61F 2013/00927; A61J 1/20–22

See application file for complete search history.

(56) References Cited

U.S. PATENT DOCUMENTS

| | | | |
|---|---|---|---|
| 9,180,142 | B2 | 11/2015 | Kushnir |
| 10,111,979 | B2 | 10/2018 | Kushnir |
| 2009/0001842 | A1 | 1/2009 | Custforth |
| 2011/0318404 | A1* | 12/2011 | Kushnir ............... A61K 9/7007<br>424/529 |
| 2013/0287837 | A1 | 10/2013 | Macphee |
| 2018/0296748 | A1* | 10/2018 | Emerson ............... A61J 1/2072 |

FOREIGN PATENT DOCUMENTS

| | | | |
|---|---|---|---|
| CN | 2776409 U | | 5/2006 |
| CN | 101155567 A | | 4/2008 |
| CN | 103480029 A | | 1/2014 |
| CN | 109847085 A | | 6/2019 |
| CN | 210990336 U | * | 7/2020 |
| EP | 2567681 A1 | | 3/2013 |
| JP | 2019528856 A | | 10/2019 |
| WO | 2019058373 A1 | | 3/2019 |
| WO | 2019058375 A1 | | 3/2019 |
| WO | 2019150355 A1 | | 8/2019 |

OTHER PUBLICATIONS

Written Opinion for corresponding application PCT/IL2021/050404 filed Apr. 7, 2021; Mail date Jun. 27, 2021.

* cited by examiner

BLOOD EXTRACTION

TECHNOLOGICAL FIELD

The present disclosure concerns a method and system for the preparation of a blood clot-based wound dressing as well as kits of parts of said system and a device useful in said method and system.

BACKGROUND

References considered to be relevant as background to the presently disclosed subject matter are listed below:
U.S. Pat. No. 9,180,142
U.S. Pat. No. 10,111,979
WO 2019/058375
WO 2019/150355

Acknowledgement of the above references herein is not to be inferred as meaning that these are in any way relevant to the patentability of the presently disclosed subject matter.

U.S. Pat. Nos. 9,180,142 and 10,111,979 disclose a wound treatment procedure by which blood is coagulated and the so-formed blood clot is applied onto a wound with a dressing material. PCT publications WO 2019/058373, WO 2019/058375 and WO 2019/150355 disclose methods, devices and systems for dressing wounds with a blood clot-comprising dressing. The blood clot-comprising dressing is, typically, prepared from blood taken from the patient. As the blood sample to be withdrawn is of a relatively small amount (as compared to that of a blood donation to a blood bank), e.g. 10-20 ml, it is typically drawn into a vacutainer (a vacuum-holding test tube that is sealed by an elastic, typically rubber, stopper) of the kind used in blood tests and then has to be withdrawn from there. As the tube is sealed, the blood withdrawal, typically with a syringe has to be against the vacuum inside the tube and this may be challenging.

GENERAL DESCRIPTION

Provided by this disclosure is a method and system for the preparation of a blood clot-based wound dressing whereby a fluid, typically gas such as air is propelled through one conduit into a sealed, blood-containing test tube, and at the same time blood is permitted to flow out of the test through a second conduit and thereby transferred into a blot clot molding space where the blood is permitted to coagulate forming a clot of a shape defined by the molding space. The propelling fluid is typically air that is propelled to flow in the first conduit by a syringe. Provide by this disclosure is also a coupling device useful in said method and system; as well as a kit of parts comprising elements needed for carrying out the method of this disclosure.

According to the method for forming a blood clot-based wound dressing of this disclosure, a blood is first accumulated in a test tube with an opening sealed by an elastic stopper (e.g. rubber stopper). This test tube is typically a vacutainer that maintains a vacuum seal inside the tube and this vacuum is the driving force for drawing blood thereinto. The blood needs then to be transferred from the test tube to a blood molding space of a mold device where the blood is permitted to clot and integrate in this process with a support matrix (which may be a wound dressing material such as gauze) that is comprised in said space, to form the blood clot-based wound dressing.

The transfer of the blood from the test tube to the molding space is by propelling a fluid (e.g. gas) into said test tube through at least one first conduit that extends through the stopper between a first distal and a first proximal end within said tube and at the same time permitting blood to flow out of the tube through at least one second conduit between a second proximal end within said tube and a second distal end. The blood egressing out of said second distal end is then channeled to and collected in said molding space.

By one embodiment, prior to said propelling and said collecting at least one first proximal elongated element defining a proximal segment of the first conduit and at least one second proximal elongated element defining a proximal segment of the second conduit is inserted through the stopper to thereby establish fluid communication between said first and said second conduits and the test tube's interior.

By one embodiment said elongated elements have each a sharp tip for penetrating through the stopper.

By one embodiment, use is made of a coupling device with said conduits being defined within the coupling device. Said elongated elements project off the device at a test tube-coupling member of the device and through proximation and engagement of the test tube and this coupling member, the elongated element pierce through the stopper to establish said fluid communication.

Said tube-coupling member may comprise a generally cylindrical receptacle with an opening and a closed end with said proximal elongated elements projecting therefrom into the receptacle. For engagement, the test tube is introduced into the cylindrical test tube receptacle with the stopper facing an end wall of said receptacle, whereupon after full insertion of the test tube into the receptacle, the two elongated elements penetrate through the stopper.

The coupling device also, typically, comprises a syringe-coupling member for coupling a syringe with said first distal end to permit to propel fluid out of the syringe and into the first conduit.

The second distal end is, typically, at an end of a tubular projection configured for piercing a wall of said molding space. The second conduit may be constituted, by some embodiments, by a metal tube integrated in the coupling device with one end projecting from the tube-coupling member and the other projecting in another (typically opposite) direction.

Said first proximal elongated element is typically longer than said second proximal elongated element. The second proximal elongated element is typically dimensioned such that after insertion through the stopper, its second proximal end is adjacent the stopper within the test tube's interior. Thus, after coupling the test tube may be positioned with its stopper-fitted end at its bottom, causing the blood to accumulate at that end and once the propelling fluid is propelled into the tube, through the first conduit, the blood is caused to flow out through the second conduit to the blood molding space. The arrangement may also be different with the second proximal elongated element being longer than the first proximal elongated element and optionally dimensioned such as to span almost the entire length of the test tube, in which case after said coupling, the test tube will be positioned with its stopper-fitted end being at the top.

The method may comprise
(i) coupling the first distal end to a syringe;
(ii) inserting the two proximal ends through the stopper into said test tube;
(iii) inserting said second distal end through a wall of said molding space;

(iv) transferring the blood from said test tube to said molding space by pushing air by the syringe into the first conduit and collecting blood in said molding space; and (v) following said collecting, maintaining the mold device such that the blood is in contact with said matrix for a time sufficient for the blood to clot to thereby obtain a wound dressing comprising a blood clot integrated with said matrix.

Steps (i), (ii) and (iii) may be performed in that or any other order.

The molding space may be of the kind disclosed in published PCT application WO 2019/058373, being an enclosure defined between walls constituted by a main body and a removable planar closure over an opening with said matrix being adjacent said closure. Said maintaining may comprise placing the mold device on its planar closure.

The second distal end may have a tip configured for piercing a wall of the mold space and prior to transfer of the blood a wall portion is pierced by said tip. Prior, during or following the transfer of the blood, a coagulation initiator may be introduced into said molding space. The coagulation initiator may be a powder or granulate matter and may comprise kaolin and/or a calcium salt (e.g. calcium gluconate).

The system of this disclosure comprises a blood collection test tube with an elastic stopper (e.g. a vacutainer), a fluid propelling device, a mold device and a coupling device. The mold device and comprises a blood-molding space with a blood clot support matrix. The fluid propelling device may be any device such as a pressurized gas canister or may also be a coupling arrangement for a central pressurized gas source. By one embodiment that fluid propelling device is a syringe and the propelling fluid is air.

The system also comprises a coupling device having a first coupling member, a second, tube-coupling member for coupling with said test tube and fluid conduits defined within the device. The fluid conduits comprise at least one first fluid conduit extending between a first distal end in the first coupling member and a first proximal end at an end of a first proximal elongated element, and at least one second fluid conduit extending between a second distal end at an end of a distal elongated element and a second proximal end at an end of a proximal elongated element. The first and the second proximal elongated elements project off the device at said tube-coupling member and are configured for piercing through said stopper. After such piercing, fluid communication is established between the conduits and the test tube's interior. The distal elongated element being configured for piercing a wall of said molding space to thereby establishing a fluid communication between said conduits and the test tube's interior. The first coupling member being configured for coupling to the fluid-propelling device in a manner permitting to propel fluid into said first conduit through said first distal end. The first coupling member has typically a female-type Luer fitment for coupling with a male-type Luer fitment of a syringe.

As noted above, this disclosure also provides a kit of parts of said system as well as a coupling device useful in said method and system.

EMBODIMENTS

The following numbered paragraph list embodiments of this disclosure. These embodiments, drafted in a claim format, are intended to add to the above general description.

1. A method for forming a blood clot-based wound dressing, comprising:
   accumulating a volume of blood in a test tube with an opening sealed by an elastic stopper (e.g. rubber stopper);
   transferring blood from the test tube to a molding space of a blood-clotting mold device, with a blood clot-support matrix within said space (e.g. a wound dressing material such as gauze), said transferring comprising
   propelling a fluid (e.g. gas) into said tube through at least one first conduit that extends through the stopper between a first distal and a first proximal end within said tube and at the same time permitting blood to flow out of the tube through at least one second conduit between a second proximal end within said tube and a second distal end, and
   collecting the blood egressing out of the second distal end in said molding space; and
   permitting the blood to clot while in contact with said matrix to thereby obtain a wound dressing comprising a blood clot integrated with said matrix.

2. A method for forming a blood clot-based wound dressing, comprising transferring an amount of blood to a molding space of a blood-clotting mold device, with a blood clot-support matrix within the space, and permitting the blood to clot while in contact with said matrix to thereby obtain a wound dressing comprising a blood clot integrated with said matrix; wherein said transferring comprises
   accumulating a volume of blood in a test tube sealed by an elastic stopper (e.g. rubber stopper), and
   propelling a fluid (e.g. gas) into said tube through at least one first conduit that extends through the stopper between the first conduit's first distal end its first proximal end within said tube and at the same time permitting blood to flow out of the tube through at least one second conduit between the second conduit's second proximal end within said tube and a second distal end, and
   collecting the blood egressing out of the second distal end in said molding space.

3. The method of embodiment 1 or 2, wherein said propelling is by a syringe coupled to said first distal end.

4. The method of any one of embodiments 1-3, comprising prior to said propelling and said collecting
   inserting, through the stopper, at least one first proximal elongated element defining a proximal segment of the first conduit and at least one second proximal elongated element defining a proximal segment of the second conduit.

5. The method of embodiment 4, wherein
   the elongated elements have each a sharp tip for penetrating through the stopper.

6. The method of embodiment 4 or 5, wherein
   said inserting comprises engaging the stopper with a tube-coupling member of a coupling device comprising said elongated elements projecting off said device, thereby causing said elements to penetrate through the stopper.

7. The method of embodiment 6, wherein
   said tube-coupling member comprises a generally cylindrical receptacle with an opening and a closed end with said proximal elongated elements projecting therefrom into the receptacle, and wherein the method comprises
   introducing the test tube into a cylindrical test tube receptacle with the stopper facing an end wall of said receptacle, whereupon after full insertion of the test tube into the receptacle, the two elongated elements penetrate through the stopper.

8. The method of embodiment 6 or 7, wherein said coupling device comprises a syringe-coupling member for coupling a syringe with said first distal end to permit to propel fluid out of the syringe and into the first conduit.

9. The method of any one of embodiments 6-8, wherein the second distal end is at an end of a tubular projection configured for piercing a wall of said molding space.

10. The method of any one of embodiments 6-9, wherein the second conduit is constituted by a metal tube integrated in the coupling device with one end projecting from the tube-coupling member and the other projecting in another (typically opposite) direction.

11. The method of any one of embodiments 4-10, wherein said first proximal elongated element is longer than said second proximal elongated element.

12. The method of any one of embodiments 1-11, comprising:
coupling the first distal end with a syringe;
inserting the two proximal ends through the stopper into said test tube;
inserting said second distal end through a wall of said molding space;
transferring the blood from said test tube to said molding space by pushing air by the syringe into the first conduit and collecting blood in said molding space; and
following said collecting, maintaining the mold device such that the blood is in contact with said matrix for a time sufficient for the blood to clot to thereby obtain a wound dressing comprising a blood clot integrated with said matrix.

13. The method of embodiment 12, wherein
said molding space is an enclosure defined between walls constituted by a main body and a removable planar closure over an opening with said matrix being adjacent said closure, and wherein
said maintaining comprises placing the mold device on its planar closure. 14. The method of embodiment 11 or 12, wherein
the second distal end has a tip configured for piercing a wall of the mold space, and wherein
said inserting comprises piercing a wall of the enclosure with said tip.

15. The method of any one of embodiments 1-14, comprising introducing a coagulation initiator into said molding space.

16. The method of embodiment 15, wherein the introduction is prior, at the same time or after said collecting.

17. The method of claim 16, wherein the coagulation initiator is a powder or granulate matter separately introduced or a priori present in said space prior to said transferring.

18. The method of embodiment 17, wherein the coagulation initiator comprises kaolin and a calcium salt (e.g. calcium gluconate).

19. The method of any one of embodiments 1-18, wherein said test tube is a vacutainer.

20. A system for forming a blood clot-based wound dressing, comprising:
a blood-collection test tube with an elastic stopper (e.g. a vacutainer);
a blood-clotting mold device defining a molding space with a blood clot-support matrix within said space;

a fluid propelling device; and
a coupling device
having a first coupling member and a second, tube-coupling member for coupling with said test tube,
fluid conduits defined in the device that comprise at least one first fluid conduit extending between a first distal end in the first coupling member and a first proximal end at an end of a first proximal elongated element, and at least one second fluid conduit extending between a second distal end at an end of a distal elongated element and a second proximal end at an end of an elongated element,
the first and second proximal elongated elements projecting off the device at said tube-coupling member and configured for piercing through said stopper,
the distal elongated element being configured for piercing a wall of said molding space, and
the first coupling member being configured for coupling to said fluid propelling device to permit said propelling device to propel fluid into said first conduit through said first distal end.

21. The system of embodiment 20, wherein said propelling device is a syringe.

22. The system of embodiment 21, wherein the proximal elongated elements have each a sharp (e.g. needle-like) tip for penetrating through the stopper.

23. The system of embodiment 21 or 22, wherein
said tube-coupling member comprises a generally cylindrical receptacle with an opening and a closed end with said proximal elongated elements projecting therefrom into the receptacle.

24. The system of any one of embodiments 20-23, wherein the second conduit is constituted by a metal tube integrated in the coupling device with a proximal segment being said second proximal elongated element and a distal segment projecting in another (typically opposite) direction.

25. The system of any one of embodiments 20-24, wherein said first proximal elongated element is longer than said second proximal elongated element.

26. The system of any one of embodiments 20-25, wherein said coupling device comprises 27. The system of any one of embodiments 20-26, wherein
said molding space is an enclosure defined between walls constituted by a main body and a removable planar closure over an opening with said matrix being adjacent said closure.

28. The system of any one of embodiments 20-27, wherein said molding space comprises a coagulation initiator.

29. The system of embodiments 28, wherein the coagulation initiator is a powder or granulate matter.

30. The system of embodiments 29, wherein the coagulation initiator comprises kaolin and a calcium salt (e.g. calcium gluconate).

31. A coupling device, comprising:
a first coupling member and a second coupling member, the first coupling member being configured for coupling with a fluid propelling device and the second coupling member being configured for coupling with a stopper-sealed test tube; and
fluid conduits defined in the device that comprise
at least one first fluid conduit extending between a first distal end in the first coupling member and a first proximal end formed at an end of a first proximal elongated element, and at least one second fluid conduit extending between a second distal end at an end of a distal elongated element and a second proximal elongated element, the first and second proximal elongated elements projecting off the device at said tube-coupling member and configured for piercing through the test-tube' stopper;

the coupling of the first coupling member with said propelling device permits fluid communication between the syringe and said first distal end; whereby upon coupling of said coupling device to said propelling device and to said test tube filled with a liquid, actuation of the propelling device propels fluid into the first conduit which in turn causes the liquid to be drained out of said test tube through said second conduit.

32. The coupling device of embodiment 31, wherein said propelling device is a syringe.

33. The coupling device of embodiment 31 or 32, wherein the elongated elements have each a sharp tip for penetrating through the stopper.

34. The coupling device of any one of embodiments 31-33, wherein said first coupling member has female-type Luer fitment for coupling with a male-type Luer fitment of a syringe.

35. The coupling device of any one of embodiments 31-34, wherein said second coupling member comprises a generally cylindrical receptacle with an opening and a closed end with the proximal elongated elements projecting therefrom into the receptacle, and wherein said cylindrical receptacle being configured for receiving the stopper-fitted end of said test tube such that the two proximal elongated elements pierce through the stopper to bring their proximal end to be within the tube.

36. The coupling device of any one of embodiments 31-35, wherein said second conduit is constituted by a metal tube integrated in the coupling device with one segment at one end constituting said second proximal elongated element and an opposite segment constituting said distal elongated element.

37. The coupling device of any one of embodiments 31-36, wherein said first proximal elongated element is longer than said second proximal elongated element.

38. The coupling device of any one of embodiments 31-37, wherein the first conduit comprises a first segment constituted by a bore in a portion of said device and extending between the first distal end in said first coupling member to a bore inner end, and a second segment constituted by a first metal tube integrated in the device and extending from said inner end to an external portion constituting said first proximal elongated element.

39. The coupling device of embodiment 38, wherein said bore linearly extend along bore axis, and said metal tube is straight and defines a tube axis angled with respect to said bore axis.

40. The coupling device of embodiment 39, wherein said second conduit is constituted by a second, straight metal tube, the second metal tube is integrated in the coupling device and is parallel to said first metal tube, and one segment at one end of said second tube constituting said second proximal elongated element and an opposite segment constituting said distal elongated element.

41. The coupling device of embodiment 40, comprising:

a central body portion accommodating said first and said second metal tube that extend along said tube axis and comprising said second coupling member;

a grip portion extending from said central body in one radial direction of said tube axis configured for holding by a user; and a syringe coupling portion extending at an opposite radial direction from said central body to said syringe-coupling member.

42. The coupling device of embodiment 41, wherein said syringe coupling portion is generally cylindrical abut said bore axis.

43. The coupling device of embodiment 41 or 42, wherein said grip portion is generally planar.

44. The coupling device of any one of embodiments 31-43, for use in the method of any one of embodiments 1-20 and the system of any one of embodiments 21-30.

45. A kit of parts comprising elements of the system of any one of embodiments 21-30.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figures 1, 2:
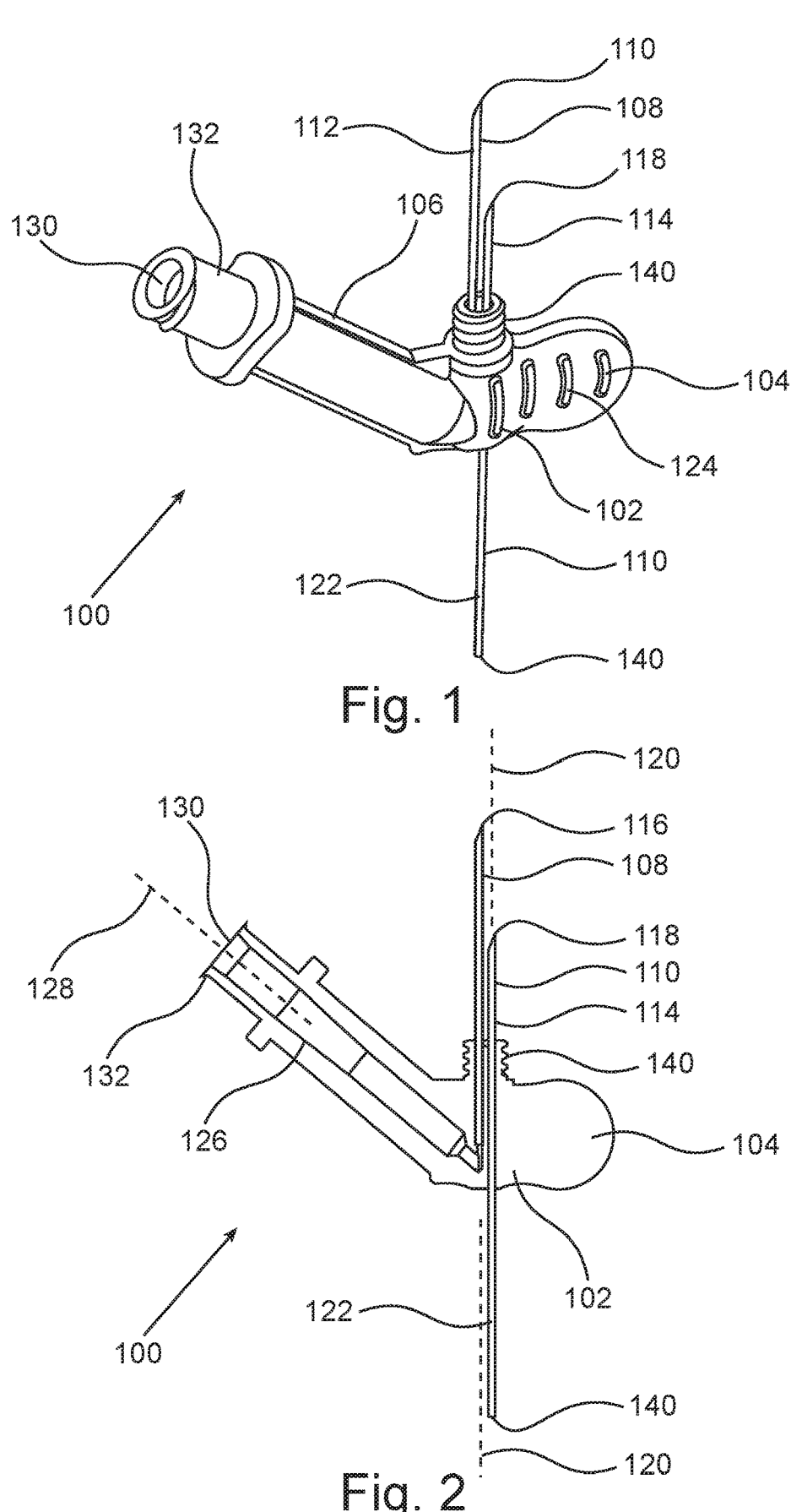
FIGS. 1 and 2 depict a perspective view and a cross-sectional view, respectively, of a coupling device of an embodiment of this disclosure.

The disclosure of this patent specification will now be illustrated in the following description. As can no doubt be understood, the embodiments illustrated below and in the annexed drawing are but exemplary to the myriad of embodiments enabled by this disclosure.

In the following text and for ease of description use will be made with "upper", "lower", "vertical", horizontal", etc. according to the orientation and relative position as depicted in the drawings. It should be understood that elements may in use, be oriented such that a "lower" element may be the upper one, a "vertical orientation may be horizontal, etc.

FIGS. 1 and 2 depict a coupling device 100 of an embodiment of this disclosure. It has a central body portion 102, a grip portion 104 and a syringe coupling portion 106.

The central body portion 102 has a general cylindrical, vertically oriented shape and accommodates a first metal tube 108, and a second metal tube 110 having upwardly projecting segments defining, respectively, a first and second elongated elements 112, 114 having, respective, needle-like tips 116, 118. Tubes 108 and 110 are parallel and extend along a vertical tube axis 120 (that is essentially also the axis defined by the cylindrical body portion 102). Tube 110 also has a downwardly projecting segment constituting a second proximal elongated element 122.

The grip portion 104 is essentially planar and extends from the central body portion 102 in one radial direction of axis 120 and the syringe coupling portion extends in the opposite direction. The grip portion is generally configured to be held or gripped by a user and the abutments 124 on its surface further adds to this function.

Defined within portion 106 is an axial bore 126, extending along a bore axis 128, in several narrowing segments, from an opening at a first distal end 130 of the bore within a first coupling member 132, being a female-type Luer fitment, to a narrow inner bore end 134. The inner end 136 of tube 108 is in fluid communication with the inner bore end 122. The bore 116 and the lumen of tube 108 constitute, together, one continuous, first conduit that extends between the first distal end 130 and a first proximal end at the needle-like tip of tube 116.

Figure 3:
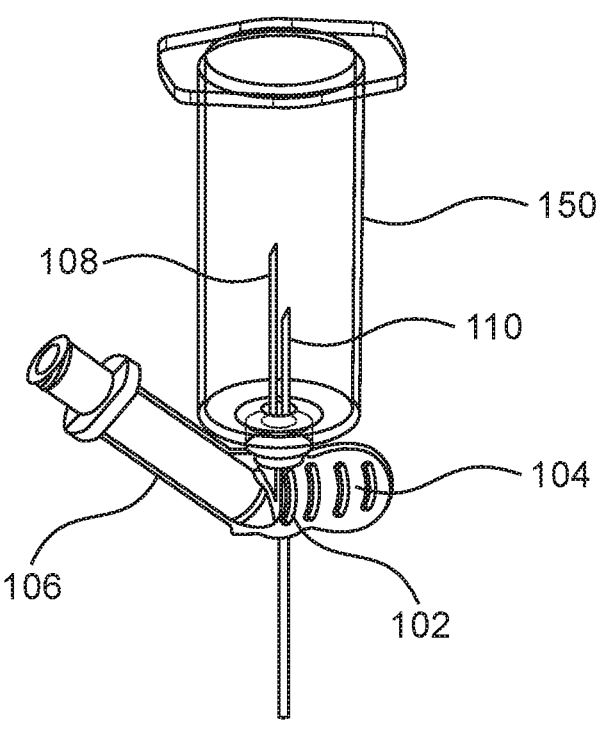
FIGS. 3 and 4 depict a perspective view and a cross-sectional view, respectively, of a coupling device such as that of FIGS. 1 and 2 with a cylindrical tube receptacle fitted at the device's tube coupling member.
Figure 4:
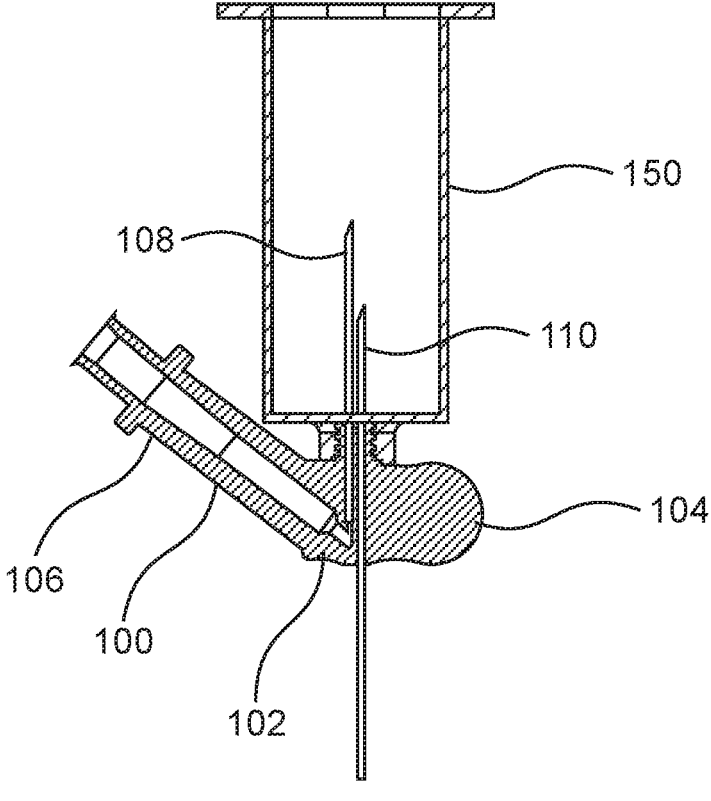

Projecting upwards from the central body is a screw-threaded member 140 with the elongated elements 112, 114 projecting upwards therefrom. Member 140 serves for engagement with the test tube, typically together with a cylindrical test-tube receptacle 150, seen in FIGS. 3 and 4, screw fitted to member 140. Receptacle 150 has an opening 152 at its top end and the two proximal elongated elements 112, 114 project into the receptacle's interior. The cylindrical receptacle 150 can receive the stopper-fitted end of the test tube whereby the two proximal elongated elements 112, 114 pierce through the stopper to bring their proximal end to be within the tube to thereby establish a fluid communication between the tubes' interior and the first and the second conduits. This will be explained below with reference to FIGS. 5-7.

Figure 5:
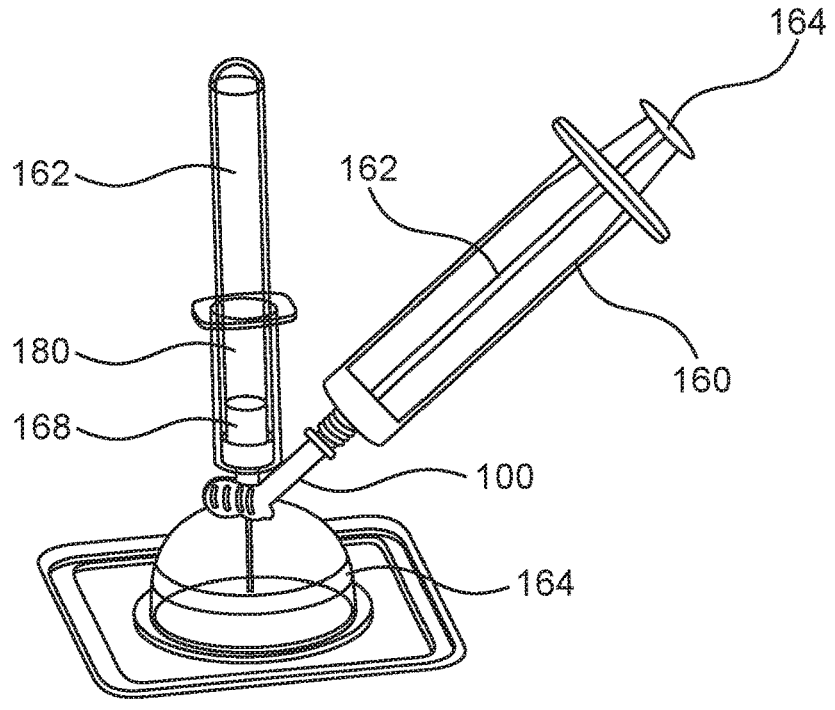
FIGS. 5, 6 and 7 respectively depict a perspective view, a partial cross-sectional view and an enlarged partial cross-sectional view of the coupling device of FIGS. 3 and 4 coupled to a vacutainer and a syringe and engaged with a mold device.
Figure 6:
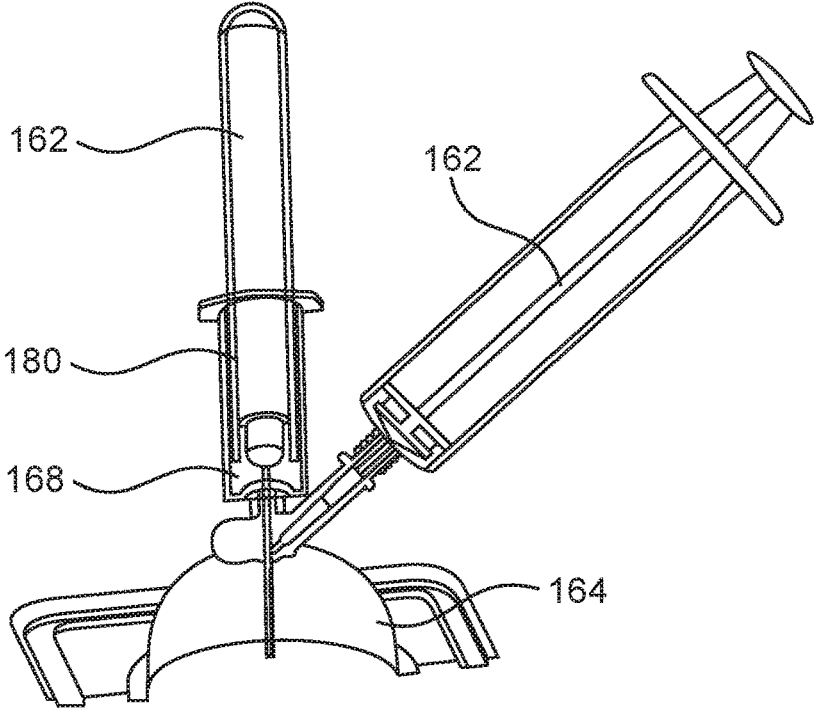
Figure 7:
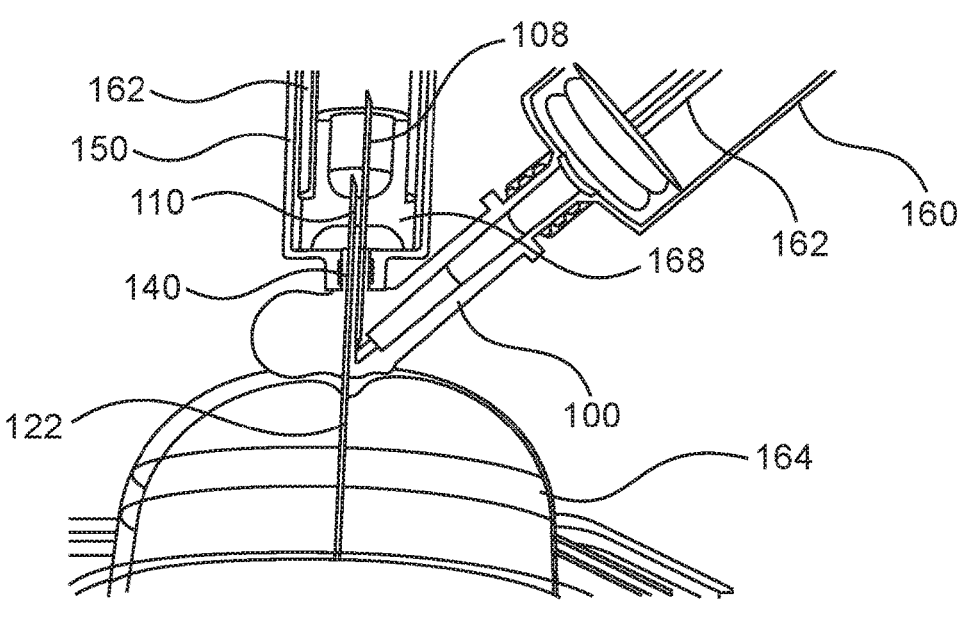

FIGS. 5-7 depicts the coupling device 100 coupled to a syringe 160, stopper-fitted test tube 162, typically a vacutainer, and also engaged with a mold device 164.

The coupling of the syringe is through a Luer-type engagement between the female-type Luer fitment of the coupling device and the counterpart mail-type Luer fitment of the syringe. Downward displacement of the syringe's plunger 162 by pressing on lever 164 will force the content of the syringe, typically air, into the distal end of the first conduit propelling the fluid content of the syringe (typically air, as aforesaid) to move through the first conduit.

Test tube 162, typically a vacutainer, has an opening fitted with a stopper 168 and for engagement, the stopper-fitted end of the test tube is inserted into the cylindrical receptacle 150 causing the two sharp tips 116, 118 to pierce through the stopper bringing their proximal end to be within the tube's interior. This causes the first and second conduits to be in fluid communication with the tube's interior. Thus, by downward displacement of the syringe's plunger, air (typically) would be forced into the first conduit, and this would cause the blood in the test tube to flow out of the second conduit. As can be seen, elongated element 108 is longer than elongated element 110, with the latter being dimensioned such that after insertion through the stopper, its second proximal end is adjacent the stopper within the test tube's interior. This will permit almost the entire blood content of the test tube to be transferred out of the second conduit.

As can also be seen in FIGS. 5-7, the second proximal elongated element 122 can be made to penetrate through a wall of a molding space 170 of a mold device and in this way the drainage of the blood out of the second conduit will cause its transfer into said space where it is permitted to clot to for a blood-clot based wound dressing in the manner disclosed in WO 2019/058373, the relevant content of which being incorporated herein by reference.

Figure 8:
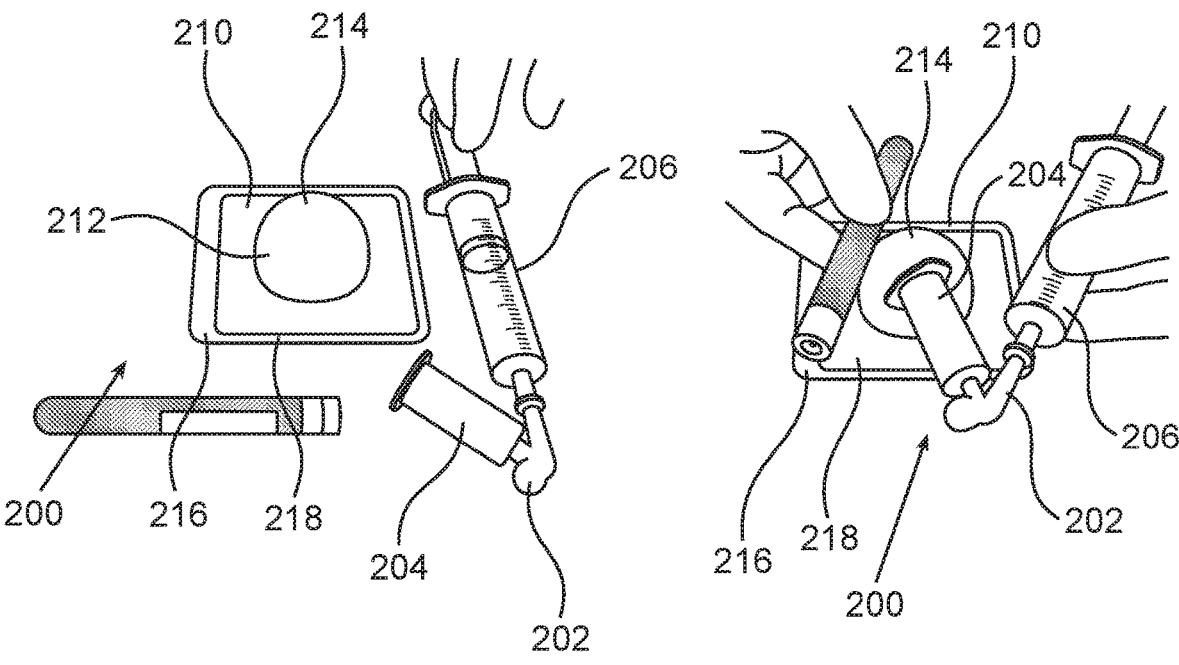
FIG. 8 depicts elements of the system of an embodiment of this disclosure.

Elements of a system 200 according to an embodiment of this disclosure are depicted in FIG. 8. It includes a coupling device 202 with a cylindrical test tube receptacle 204 coupled to a syringe 206, a vacutainer 208, already filled with blood withdrawn from a patient and a mold device 210 with a blood molding space 212, being an enclosure define between walls 214 and a removable planar closure 216. The mold device 210 also included a piece of gauze 218 that lies adjacent the closure and a portion of it is within the enclosure. For preparation of the blood clot-based wound dressing the blood is introduced into the space 212 and then permitted to clot when the mold is placed on its planar closure causing the forming blood clot to integrate with the gauze to form the wound dressing.

The sequence of steps in carrying out the method according to an embodiment of this disclosure is depicted in FIGS. 9B-9F. It should be noted that this sequence of steps is exemplary. For example, rather than as shown, the coupling device can first be coupled with the blood-containing vacutainer and only then engaged with the mold device.

Figure 9A:
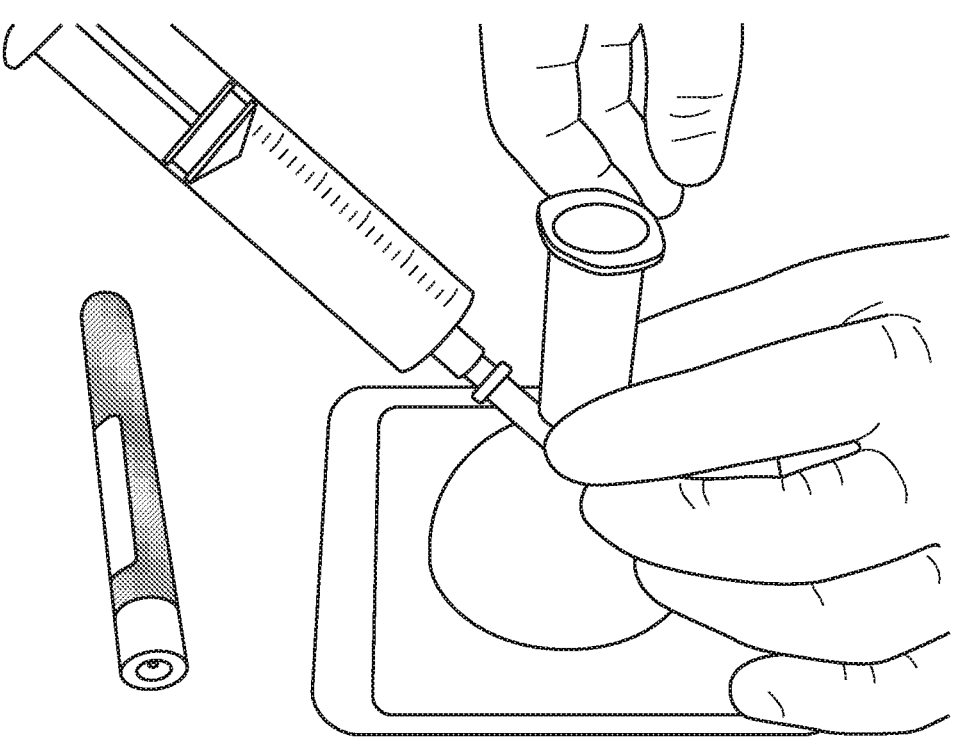
FIGS. 9A-9F depict a sequence of steps in carrying out the method according to an embodiment of this disclosure.
Figure 9B:
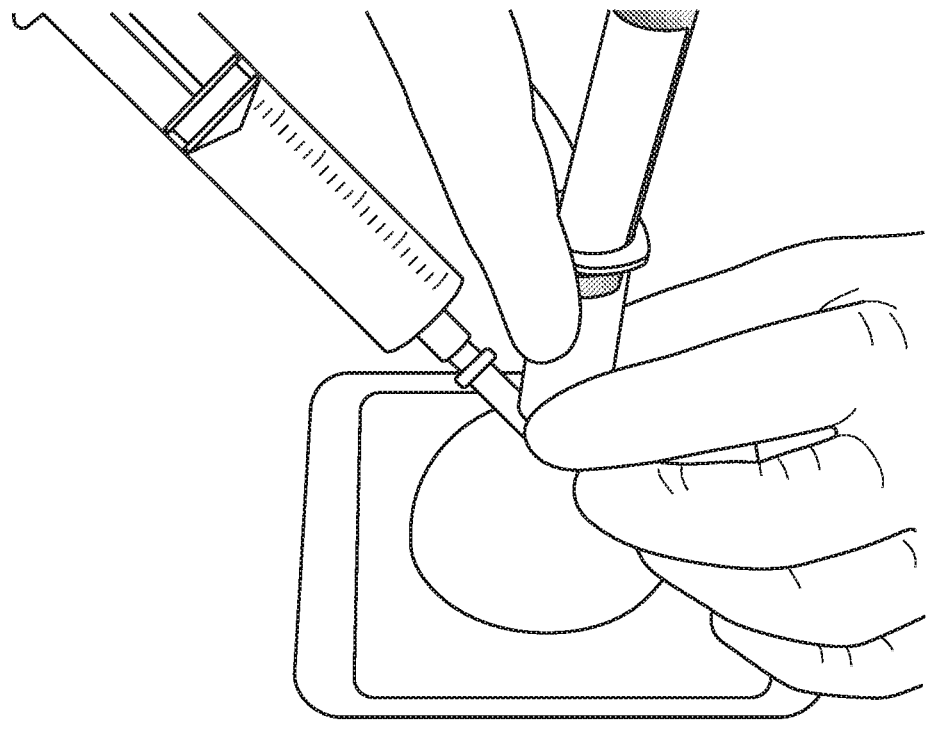
Figure 9C:
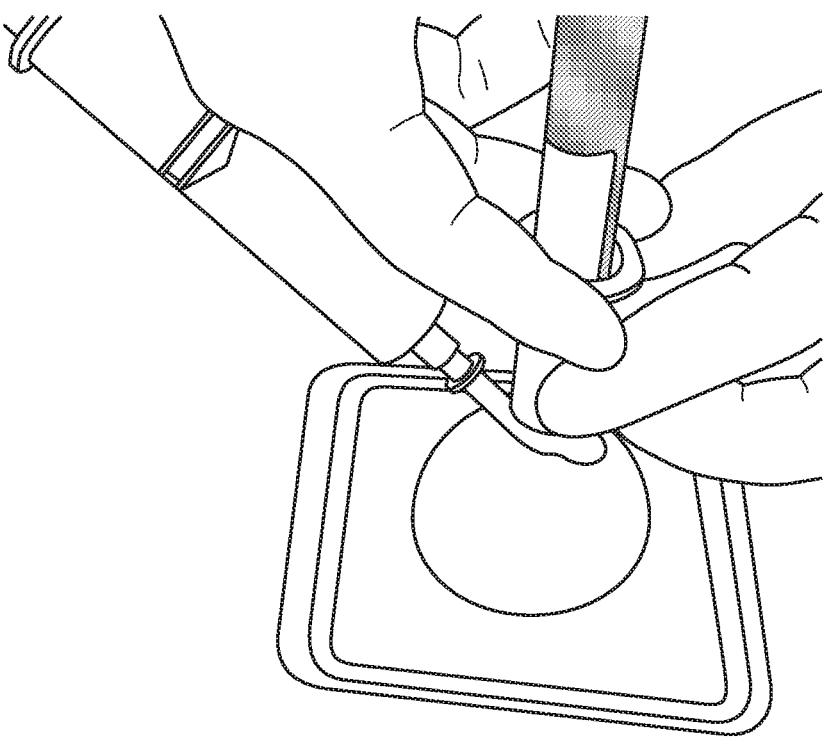
Figure 9D:
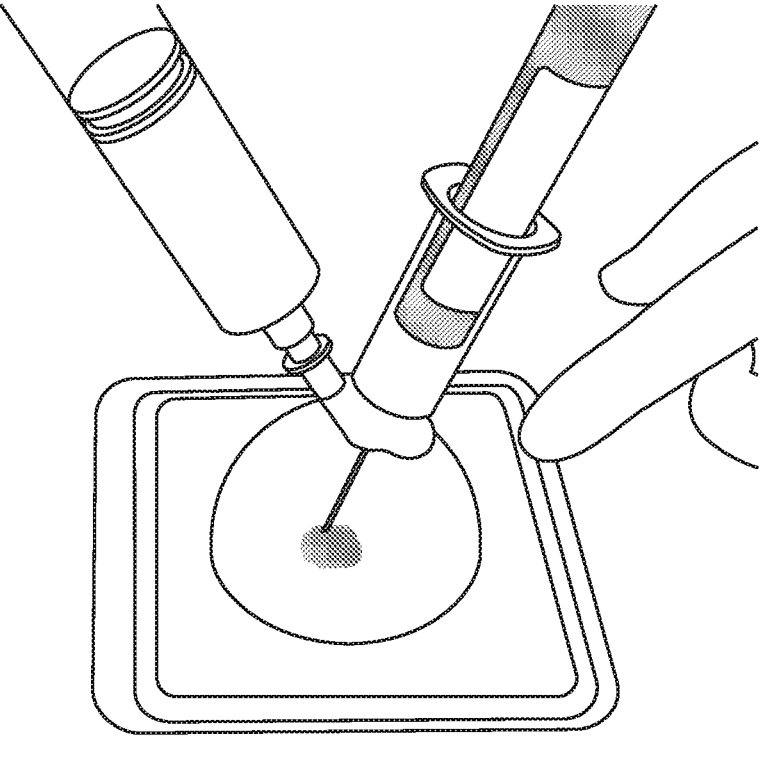
Figure 9E:
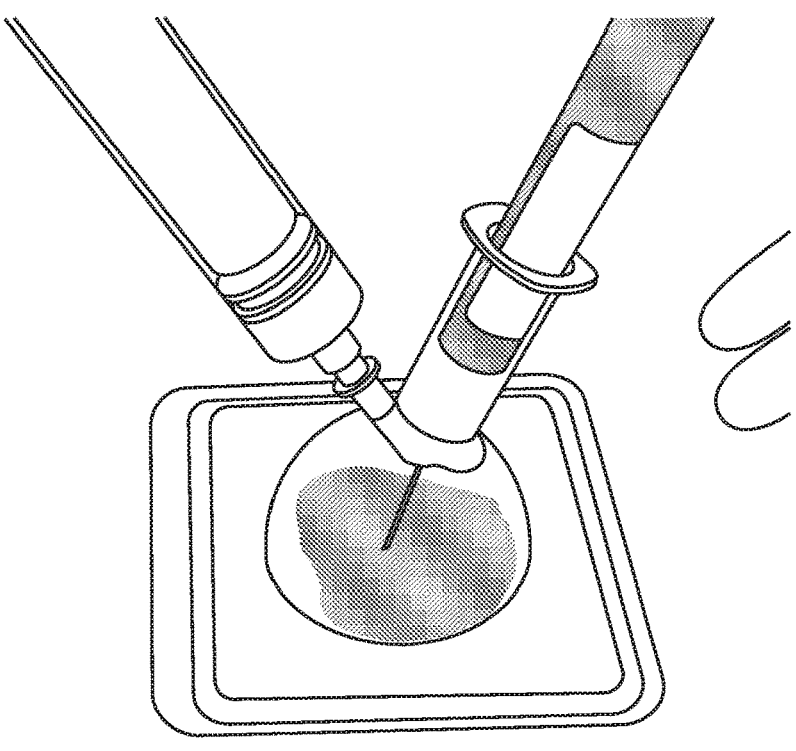
Figure 9F:
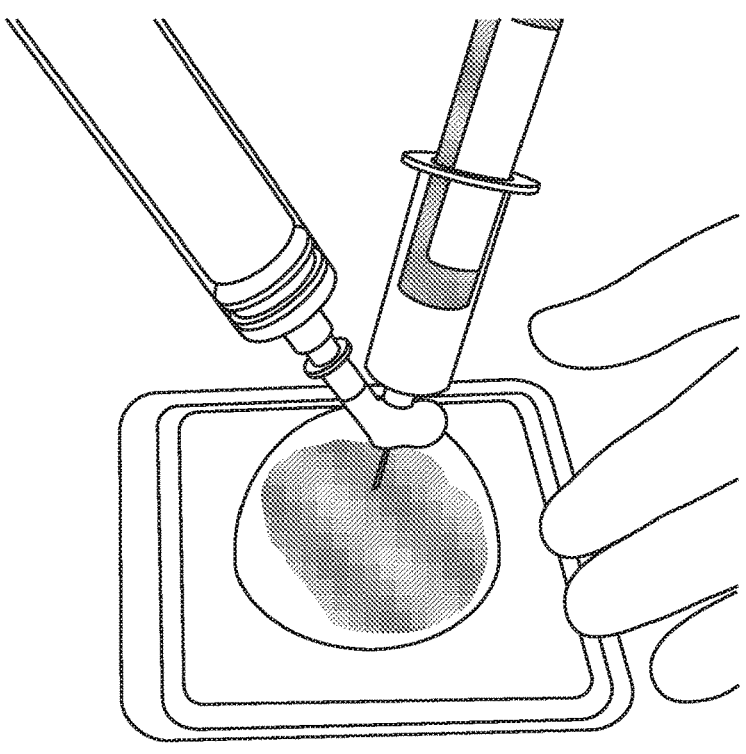

FIG. 9A shows engagement of the coupling device with the syringe attached t the mold device, which is done by piercing a wall of the molding space with the second proximal elongated element of the coupling device (not see in this figure). Then a vacutainer filled with blood is coupled in the manner described above (FIGS. 9B-9C) and then the syringe's plunger is displaced causing the blood to transfer from the vacutainer to the molding space (FIGS. 9D-9F). Following incubation to permit clotting of blood, typically using blood coagulation inducers, a priori present in said space or introduced prior, during or following the blood introduction into said space.

The invention claimed is:

1. A method for forming a blood clot-based wound dressing, comprising:
   accumulating a volume of blood in a test tube with an opening sealed by an elastic stopper;
   transferring blood from the test tube to a molding space of a blood-clotting mold device, with a blood clot-support matrix within said space, said transferring comprising propelling a fluid into said tube through at least one first conduit that extends through the stopper between a first distal and a first proximal end within said tube and at the same time permitting blood to flow out of the tube through at least one second conduit between a second proximal end within said tube and a second distal end, and
   collecting the blood egressing out of the second distal end in said molding space; and
   permitting the blood to clot while in contact with said matrix to thereby obtain a wound dressing comprising a blood clot integrated with said matrix.

2. The method of claim 1, wherein said propelling is by a syringe coupled to said first distal end.

3. The method of claim 1, comprising prior to said propelling and said collecting
   inserting, through the stopper, at least one first proximal elongated element defining a proximal segment of the first conduit and at least one second proximal elongated element defining a proximal segment of the second conduit;
   wherein the elongated elements have each a sharp tip for penetrating through the stopper.

4. The method of claim 3, wherein said first proximal elongated element is longer than said second proximal elongated element.

5. The system of claim 4, wherein said propelling device is a syringe.

6. The method of claim 3, wherein said inserting comprises engaging the stopper with a tube-coupling member of a coupling device comprising said elongated elements projecting off said device, thereby causing said elements to penetrate through the stopper.

7. The method of claim 6, wherein said tube-coupling member comprises a generally cylindrical receptacle with an opening and a closed end with said proximal elongated elements projecting therefrom into the receptacle, and wherein the method comprises introducing the test tube into a cylindrical test tube receptacle with the stopper facing an end wall of said receptacle, whereupon after full insertion of the test tube into the receptacle, the two elongated elements penetrate through the stopper; wherein said coupling device comprises a syringe-coupling member for coupling a syringe with said first distal end to permit to propel fluid out of the syringe and into the first conduit.

8. The method of claim 6, wherein the second distal end is at an end of a tubular projection configured for piercing a wall of said molding space; and wherein the second conduit is constituted by a metal tube integrated in the coupling device with one end projecting from the tube-coupling member and the other projecting in another direction.

9. The method of claim 1, comprising:

coupling the first distal end with a syringe;

inserting the two proximal ends through the stopper into said test tube;

inserting said second distal end through a wall of said molding space;

transferring the blood from said test tube to said molding space by pushing air by the syringe into the first conduit and collecting blood in said molding space; and following said collecting, maintaining the mold device such that the blood is in contact with said matrix for a time sufficient for the blood to clot to thereby obtain a wound dressing comprising a blood clot integrated with said matrix.

10. A method for forming a blood clot-based wound dressing, comprising transferring an amount of blood to a molding space of a blood-clotting mold device, with a blood clot-support matrix within the space, and permitting the blood to clot while in contact with said matrix to thereby obtain a wound dressing comprising a blood clot integrated with said matrix; wherein said transferring comprises accumulating a volume of blood in a test tube sealed by an elastic stopper, and propelling a fluid into said tube through at least one first conduit that extends through the stopper between the first conduit's first distal end its first proximal end within said tube and at the same time permitting blood to flow out of the tube through at least one second conduit between the second conduit's second proximal end within said tube and a second distal end, and collecting the blood egressing out of the second distal end in said molding space.

11. A system for forming a blood clot-based wound dressing, comprising:

a blood-collection test tube with an elastic stopper;

a blood-clotting mold device defining a molding space with a blood clot-support matrix within said space;

a fluid propelling device; and a coupling device having a first coupling member and a second, tube-coupling member for coupling with said test tube, fluid conduits defined in the device that comprise at least one first fluid conduit extending between a first distal end in the first coupling member and a first proximal end at an end of a first proximal elongated element, and at least one second fluid conduit extending between a second distal end at an end of a distal elongated element and a second proximal end at an end of an elongated element, the first and second proximal elongated elements projecting off the device at said tube-coupling member and configured for piercing through said stopper, the distal elongated element being configured for piercing a wall of said molding space, and the first coupling member being configured for coupling to said fluid propelling device to permit said propelling device to propel fluid into said first conduit through said first distal end.

12. A coupling device, comprising:

a first coupling member and a second coupling member, the first coupling member being configured for coupling with a fluid propelling device and the second coupling member being configured for coupling with a stopper-sealed test tube; and fluid conduits defined in the device that comprise at least one first fluid conduit extending between a first distal end in the first coupling member and a first proximal end formed at an end of a first proximal elongated element, and at least one second fluid conduit extending between a second distal end at an end of a distal elongated element and a second proximal elongated element, the first and second proximal elongated elements projecting off the device at said tube-coupling member and configured for piercing through the stopper of the test tube;

the coupling of the first coupling member with said propelling device permits fluid communication between the fluid propelling device and said first distal end; whereby upon coupling of said coupling device to said propelling device and to said test tube filled with a liquid, actuation of the propelling device propels fluid into the first conduit which in turn causes the liquid to be drained out of said test tube through said second conduit; wherein said propelling device is a syringe; wherein the elongated elements have each a sharp tip for penetrating through the stopper.

13. The coupling device of claim 12, wherein said first coupling member has female-type Luer fitment for coupling with a male-type Luer fitment of a syringe.

14. The coupling device of claim 12, wherein said second coupling member comprises a generally cylindrical receptacle with an opening and a closed end with the proximal elongated elements projecting therefrom into the receptacle, wherein said cylindrical receptacle being configured for receiving the stopper-fitted end of said test tube such that the two proximal elongated elements pierce through the stopper to bring their proximal end to be within the tube.

15. The coupling device of claim 12, wherein said second conduit is constituted by a metal tube integrated in the coupling device with one segment at one end constituting said second proximal elongated element and an opposite segment constituting said distal elongated element.

16. The coupling device of claim 12, wherein said first proximal elongated element is longer than said second proximal elongated element; wherein the first conduit comprises a first segment constituted by a bore in a portion of said device and extending between the first distal end in said first coupling member to a bore inner end, and a second segment constituted by a first metal tube integrated in the device and extending from said inner end to an external portion constituting said first proximal elongated element; wherein said bore linearly extend along bore axis, and said metal tube is straight and defines a tube axis angled with respect to said bore axis.

17. The coupling device of claim 16, wherein said second conduit is constituted by a second, straight metal tube, the second metal tube is integrated in the coupling device and is parallel to said first metal tube, and one segment at one end of said second tube constituting said second proximal elongated element and an opposite segment constituting said distal elongated element; wherein the device further comprising: a central body portion accommodating said first and said second metal tube that extend along said tube axis and comprising said second coupling member; a grip portion extending from said central body in one radial direction of said tube axis configured for holding by a user; and a syringe coupling portion extending at an opposite radial direction from said central body to said syringe-coupling member.

18. The coupling device of claim 17, wherein said syringe coupling portion is generally cylindrical abut said bore axis and said grip portion is generally planar.

19. A coupling device, comprising:

a first coupling member and a second coupling member, the first coupling member being configured for coupling with a fluid propelling device and the second coupling member being configured for coupling with a stopper-sealed test tube; and fluid conduits defined in the device that comprise at least one first fluid conduit extending between a first distal end in the first coupling member and a first proximal end formed at an end of a first proximal elongated element, and at least one second fluid conduit extending between a second distal end at an end of a distal elongated element and a second proximal elongated element, the first and second proximal elongated elements projecting off the device at said tube-coupling member and configured for piercing through the stopper of the test tube;

the coupling of the first coupling member with said propelling device permits fluid communication between the fluid propelling device and said first distal end; whereby upon coupling of said coupling device to said propelling device and to said test tube filled with a liquid, actuation of the propelling device propels fluid into the first conduit which in turn causes the liquid to be drained out of said test tube through said second conduit; wherein said first coupling member has female-type Luer fitment for coupling with a male-type Luer fitment of a syringe.

* * * * *